(12) United States Patent
Eckstein et al.

(10) Patent No.: US 9,417,169 B2
(45) Date of Patent: Aug. 16, 2016

(54) SENSOR ARRANGEMENT, FOR EXAMPLE, ON AN ANCHOR BOLT

(75) Inventors: Andreas Eckstein, Landsberg (DE); Mathias Goldt, Feldkirch (AT); Marc Schaeffer, Feldkirch-Nofels (AT); Joerg Appl, Feldkirch (AT); Arjen Detmer Dijkhuis, Feldkirch (AT); Matthias Paetow, Landsberg am Lech (DE)

(73) Assignee: Hilti Aktiengesellschaft, Schaan (LI)

( * ) Notice: Subject to any disclaimer, the term of this patent is extended or adjusted under 35 U.S.C. 154(b) by 31 days.

(21) Appl. No.: 13/878,696

(22) PCT Filed: Aug. 24, 2011

(86) PCT No.: PCT/EP2011/064510
§ 371 (c)(1),
(2), (4) Date: Jul. 30, 2013

(87) PCT Pub. No.: WO2012/048933
PCT Pub. Date: Apr. 19, 2012

(65) Prior Publication Data
US 2013/0298687 A1 Nov. 14, 2013

(30) Foreign Application Priority Data
Oct. 11, 2010 (DE) .......................... 10 2010 042 263

(51) Int. Cl.
*F16B 31/02* (2006.01)
*G01N 3/22* (2006.01)
*F16B 13/06* (2006.01)

(52) U.S. Cl.
CPC ............... *G01N 3/22* (2013.01); *F16B 13/065* (2013.01); *F16B 31/028* (2013.01); *F16B 2031/022* (2013.01)

(58) Field of Classification Search
CPC ............. F16B 13/065; F16B 2031/022; F16B 31/028; F16B 1/0071; F16B 13/0858; F16B 43/00; G01N 3/22; G01L 5/243
USPC ....................................... 73/761; 411/378, 411
See application file for complete search history.

(56) References Cited

U.S. PATENT DOCUMENTS

| | | | |
|---|---|---|---|
| 7,021,153 B2 * | 4/2006 | Almanstoetter et al. ........ 73/761 |
| 2007/0014490 A1 | 1/2007 | Silverbrook et al. | |
| 2010/0260013 A1 * | 10/2010 | Bedwell ........................ 367/149 |

FOREIGN PATENT DOCUMENTS

| | | |
|---|---|---|
| DE | 10316632 B4 | 9/2005 |
| DE | 102004033813 | 2/2006 |
| GB | 2263526 | 7/1993 |
| JP | H05263857 | 10/1993 |
| JP | 2002236064 | 8/2002 |
| JP | 2010127298 | 6/2010 |
| WO | WO2007/070933 | 6/2007 |
| WO | WO 2007070933 A1 * | 6/2007 |

* cited by examiner

*Primary Examiner* — Lisa Caputo
*Assistant Examiner* — Brandi N Hopkins
(74) *Attorney, Agent, or Firm* — Davidson, Davidson & Kappel, LLC

(57) ABSTRACT

A sensor arrangement, for example, on an anchor bolt, including at least one sensor (10). At least one bypass element (20) with a dilatant material is arranged in the area of the sensor (10), whereby impact forces that act upon the sensor (10) can be dissipated via the dilatant material of the bypass element (20).

5 Claims, 1 Drawing Sheet

SENSOR ARRANGEMENT, FOR EXAMPLE, ON AN ANCHOR BOLT

The invention relates to a sensor arrangement, for example, on an anchor bolt.

BACKGROUND

German patent specification DE 103 16 632 B4, for instance, discloses a screw bolt having a so-called load-indicator disk, also referred to as a "direct tension indicator" (DTI). Such an indicator has sensors for checking the tension set on the screw bolt, whereby the sensors consist of capsules that are filled with a dye. At a predefined axial load, the dye comes out of the indicator and/or becomes visible at the edge of the indicator. Therefore, the sensors can confirm that the target tension has been reached without the need to detect the installation torque.

SUMMARY OF THE INVENTION

However, it has been found that, at times, direct tension indicators do not function reliably when they are employed in concrete anchors.

It is an object of the present invention to provide a particularly reliable sensor arrangement.

The present invention provides that at least one bypass element with a dilatant material is arranged in the area of the sensor, whereby impact forces that act upon the sensor can be dissipated via the dilatant material.

The invention is based on the insight that the difficulties that are sometimes encountered when direct tension indicators are used on concrete anchors can be ascribed to the hammering step that is normally needed with concrete anchors. During the hammering step, high impact forces act upon the anchor and thus also on the direct tension indicator. These impact forces can damage or at least weaken the dye-filled capsules that serve as sensors. This can especially cause the dye to be discharged prematurely, so that it is no longer possible to correctly check the tension when the anchor is being tightened.

The present invention provides for at least one bypass element that at least partially dissipates the impact forces that occur during the hammering step, thus relieving the pressure on the sensor and protecting it. The bypass element here has a dilatant material, at least in certain areas, by means of which the impact forces are dissipated. Such a dilatant material is characterized in that it resists deformation if a force is applied over a short period of time, for instance, less than 0.1 seconds, and yet it is deformable if the force is applied for a longer period of time of, for example, more than 3 seconds. In this manner, the dilatant material can absorb forces of short duration such as those that occur due to hammer strikes, and can cause them to bypass the sensor, thus protecting it. If, in contrast, the forces act over a longer period of time such as, for example, when the screw bolt is being tensioned, the dilatant material yields, so that the forces are not dissipated by the bypass element, but rather, act upon the sensor.

According to the invention, the sensor is thus protected against force peaks while forces of a longer duration can be indicated by the sensor. In particular, it is possible to hammer in bolts having direct tension indicators without activating the direct tension indicators during the hammering step, since the bypass element causes the impact forces that occur during the hammering to bypass the sensor indicator. The bypass element and the dilatant material are thus advantageously connected in parallel in terms of the force.

Fundamentally, the invention can be employed in any desired sensors, whereby the term "sensor" refers to any device that detects a primary quantity and converts it into an output quantity. In particular, however, the sensor can be the dye capsule of a direct tension indicator, whereby in this case, the primary quantity is the axial load onto the indicator and the output quantity is the coloration. The invention, however, can also be used to protect electronic sensors that deliver electronic output quantities.

It is especially preferred that a first part is provided on which the sensor is arranged, and a second part that can be moved in an axial direction relative to the first part, whereby the sensor and the dilatant material are arranged between the two parts, as seen in the axial direction. This translates into a particularly compact arrangement. Since the sensor and the dilatant material are arranged adjacent and parallel to each other in terms of the force, the dilatant material can absorb axially directed impacts and cause them to bypass the sensor. When the application involves use on a screw bolt, especially on an anchor, it can be provided that the first part is a washer and/or the second part is a screw nut.

In particular, it is advantageous that the sensor is configured on a direct tension indicator and that it preferably consists of at least one indicator capsule. In this case, the first part is the direct tension indicator.

BRIEF DESCRIPTION OF THE DRAWINGS

The invention will be explained in greater detail below on the basis of preferred embodiments. The following is shown.

DETAILED DESCRIPTION

Figure 1:
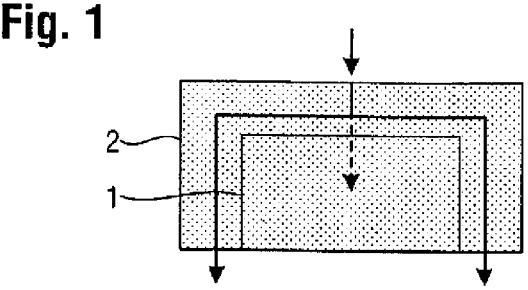
FIG. 1: a cross-sectional view of a first embodiment of a sensor arrangement according to the invention.

FIG. 1 shows a first embodiment of a sensor arrangement according to the invention. The arrangement shows a sensor 1 that can be configured, for instance, mechanically or even electrically. Moreover, the arrangement has a bypass element 2 that is made of a dilatant material. The sensor 1 is embedded into this material, whereby the dilatant material runs on the top of the sensor I as well as along its two sides. If an impact is now applied from the top onto the sensor arrangement of FIG. 1, the appertaining force, as shown by solid arrows in FIG. 1, is absorbed by the dilatant material of the bypass element 2 and dissipated on both sides of the sensor 1. The sensor 1, in contrast, is only loaded slightly or not at all.

If, on the other hand, the force acts from the top for a longer period of time, then the dilatant material can be deformed and the force acting from the top, as shown with a broken-line arrow in FIG. 1, can act upon the sensor 1 and can be detected by it. Thus, on the one hand, the sensor 1 can detect forces acting from the top, provided that they are of a longer duration, and, on the other hand, it is protected by the bypass element 2 against brief impacts from the top.

Figure 2:
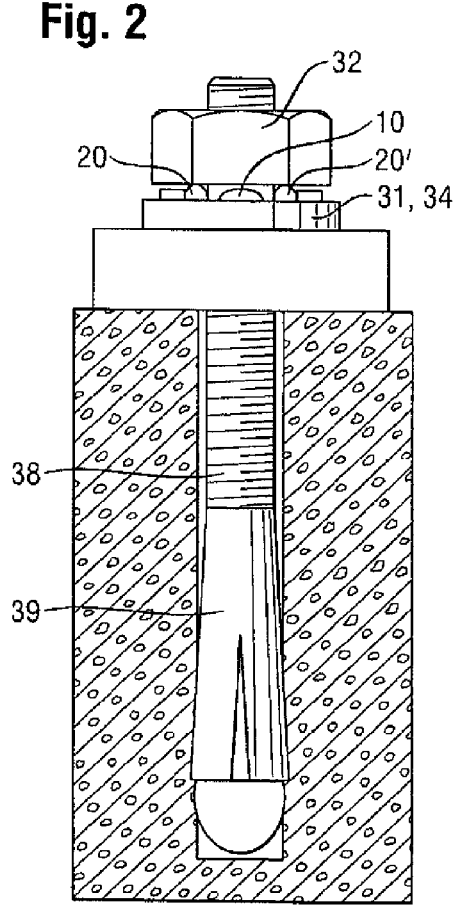
FIG. 2: a cross-sectional view of a second embodiment of a sensor arrangement according to the invention, on an anchor bolt configured as a concrete anchor.
Figure 3:
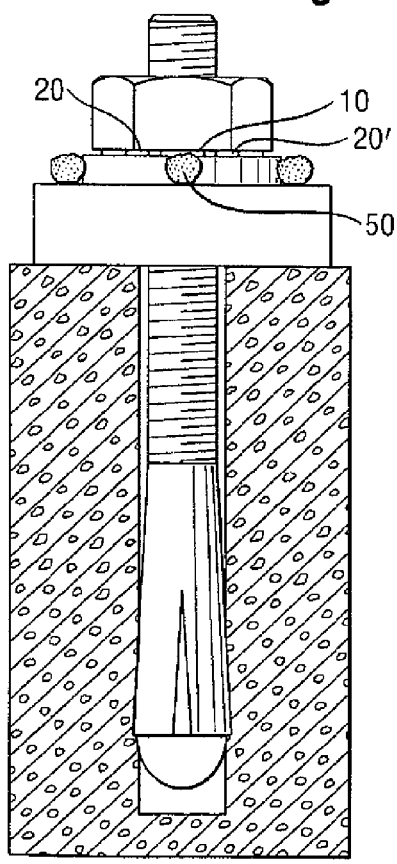
FIG. 3: the embodiment from FIG. 2, after activation of the direct tension indicator.

FIGS. 2 and 3 show an application of a sensor arrangement according to the invention, on an anchor bolt that is configured as a concrete anchor. The anchor bolt has a screw bolt 38 on one end area of which there is a conventional expansion element 39. The opposite end area of the screw bolt 38 passes through a washer 31 and the screw bolt 38 also has a screw nut 32 that is arranged above the washer 31.

On the side of the washer 31 facing the screw nut 32, the screw nut 32 has at least one indicator capsule filled with a dye, forming a force sensor 10. If the screw nut 32 is tightened when the anchor bolt is installed, the screw nut 32 comes into contact with the sensor 10. If the screw nut 32 is tightened further, the screw nut 32 exerts an ever-greater force that acts from the top onto the adjacent sensor 10 and that corresponds to the pre-tension in the screw bolt 38. When the force being exerted on the sensor 10 ultimately reaches a predefined threshold value, then a mechanical element on the sensor 10 yields and dye 50 can be discharged from the indicator capsule out of the sides of the washer 31, as shown in FIG. 3. This can serve as an indication that a desired target tension has been reached in the screw bolt 38. Therefore, the washer 31, together with the sensor 10 configured as an indicator capsule, forms a direct tension indicator 34.

As further shown in FIGS. 2 and 3, the sensor arrangement also has bypass elements 20, 20' that are made of a dilatant material. The bypass elements 20, 20' are arranged on the washer 31 next to the sensor 10. As is the case with the sensor 10, the bypass elements 20, 20' are located between the screw nut 32 and the washer 31, so that an axial force brought to bear by the screw nut can act upon the sensor 10 as well as upon the bypass elements 20, 20'.

If an impact is then applied onto the screw bolt 38 and thus onto the screw nut 32, for instance, when the anchor bolt is hammered in, this impact is transferred by the screw nut 32 to the bypass elements 20, 20'. Due to the brief nature of the impact, the dilatant bypass elements 20, 20' are at most only negligibly deformed during the impact, so that the impact force can be transferred directly to the adjacent washer 31. Therefore, the bypass elements 20, 20' cause the impact force to bypass the sensor 10. If, in contrast, the axial force acts for a longer period of time, for instance, when the screw nut 32 is being tightened, then the bypass elements 20, 20' can be deformed and the axial force can then act upon the sensor 10, so that the sensor 10 can absorb this force and display it as depicted in FIG. 3.

What is claimed is:

1. An anchor bolt comprising:
   a screw bolt and an expansion element on one end of the screw bolt, an opposite end of the screw bolt passing through a washer,
   a screw nut being arranged above the washer, and
   a sensor arrangement being arranged between the screw nut and the washer, the sensor arrangement including at least one sensor and at least one bypass element with a dilatant material arranged in the area of the sensor, impact forces acting upon the sensor capable of being dissipated via the dilatant material of the bypass element wherein the dilatant material runs on a top of the sensor and along two sides of the sensor and extends on the two sides fully between the screw nut and the washer.

2. The anchor bolt as recited in claim 1 wherein the sensor is embedded in the dilatant material.

3. The anchor bolt as recited in claim 1 wherein the sensor together with the washer defines a direct tension indicator.

4. The anchor bolt as recited in claim 1 wherein the sensor includes at least one indicator capsule.

5. The anchor bolt as recited in claim 1 wherein the dilatant material has a higher deformation resistance for forces applied over less than 0.1 seconds than for forces applied for more than 3 seconds.

* * * * *